US005482040A

United States Patent [19]
Martin, Jr.

[11] Patent Number: 5,482,040
[45] Date of Patent: Jan. 9, 1996

[54] BIOSTAGING OF ADENOCARCINOMAS UTILIZING RADIOLABELED TUMOR-ASSOCIATED GLYCOPROTEIN ANTIBODIES

[75] Inventor: Edward W. Martin, Jr., Delaware, Ohio

[73] Assignee: The Ohio State University Research Foundation, Columbus, Ohio

[21] Appl. No.: 227,447

[22] Filed: Apr. 14, 1994

[51] Int. Cl.$^6$ .................................................. A61B 6/00
[52] U.S. Cl. ................... 128/653.1; 128/654; 424/1.49; 424/1.53
[58] Field of Search ............................. 128/653.1, 654; 424/1.49, 1.53

[56] References Cited

U.S. PATENT DOCUMENTS

| | | | |
|---|---|---|---|
| 4,361,644 | 11/1982 | Goldenberg | 424/1.49 |
| 4,444,744 | 4/1984 | Goldenberg | 424/1.49 |
| 4,782,840 | 11/1988 | Martin, Jr. et al. | 128/654 |
| 4,889,991 | 12/1989 | Ramsey et al. | 128/659 |
| 5,008,546 | 4/1991 | Mazziotta et al. | 250/366 |
| 5,171,666 | 12/1992 | Gutowski et al. | 530/388.85 |
| 5,383,456 | 1/1995 | Arnold et al. | 128/653.1 |

FOREIGN PATENT DOCUMENTS

| 8004537 | 6/1988 | WIPO | 424/1.49 |
|---|---|---|---|

OTHER PUBLICATIONS

Nieroda et al., Radioimmunoguided Surgery in Colorectal Cancer, 1991, V15,N3,P225–229.
Stella et al., Avidin–Biotin System in RIGS for Colorectal–Cancer, Apr. 1994,V37,N4,P335–343.
Hand et al., Potential for Recombinant Immunoglobulin Constructs . . . , Feb. 1994,V73,N3,P1105–1113.
Triozzi et al., Localization of . . . Lymph–node Lymphocytes using . . . Mab,Feb. 1994,V73,N3,P580–589.
Stella et al., Surgery for Colorectal Cancer Guided by Radiodetecting Probe . . . , 1991, V157,N8,P485–488.
Greiner et al., Applications for Mab and Recombinant Cytokines . . . , 1991,S2,P9–13.
Dawson et al., The Value of RIGS in 1st and 2nd Look Laparotomy for Cancer, 1991,V34,N3,P217–222.

Primary Examiner—William E. Kamm
Assistant Examiner—Brian L. Casler
Attorney, Agent, or Firm—Mueller and Smith

[57] ABSTRACT

Broadly, the present invention is directed to a method for reliably staging adenocarcinomas typified by colorectal cancer in patients who are undergoing surgery therefor. The method includes the administration of a radiolabeled tumor-associated glycoprotein (TAG) antibody (or other equivalent locator) to the cancer patient prior to surgical accession of the patient. Desirably, the present method includes surgical accession with a radiation detection probe for determining tissue exhibiting elevated levels of radiation. The preferred radiolabel is $^{125}I$, which is used to label an antibody specific to a high molecular weight glycoprotein called TAG-72. The preferred antibody is CC49, a murine monoclonal antibody of the $IgG_1$ subclass. With radiolabeled monoclonal antibody CC49, it preferably is administered to the patient approximately 21 days (±4 days) prior to surgery. Following surgical excision of all such tissue which is amenable to excision, the probe is again used to identify any remaining neoplastic tissue or tissue deposits, which may or may not be subjected to further excision attempts. After all possible excision of neoplastic tissue has occurred, final counts are taken with the probe to identify residual tissue deposits not excised. The number and location of the remaining tissue deposits form the basis of the biostaging system disclosed herein.

20 Claims, 9 Drawing Sheets

ZONES

FINAL RIGS NUMBER

FIG. 4      N = 86

BIOSTAGING OF ADENOCARCINOMAS UTILIZING RADIOLABELED TUMOR-ASSOCIATED GLYCOPROTEIN ANTIBODIES

BACKGROUND OF THE INVENTION

The present invention broadly relates to the staging of cancer and more particularly to the biostaging of adenocarcinomas typified by colorectal adenocarcinomas (colorectal cancer) utilizing radiolabeled TAG antibodies. While the present invention has applicability to a adenocarcinoma in general, the invention will be particularly illustrated by description of colorectal cancer. Such illustrative description is by no means a limitation on the present invention.

Cancer of the large bowel, i.e., the colon or rectum, affects about one person in 20 in the United States and in most Westernized countries. With more than 155,000 new cases diagnosed in the United States each year, representing 15% of all cancers, this disease constitutes a major public health problem. Efforts at earlier diagnosis and the control of metastatic disease have reduced somewhat the overall death rate from colorectal cancer in recent years. The 5-year relative survival rate from colon cancer increased from 41% in the 1950's to 54% in the 1980's, and the rate for rectal cancer increased from 40% to 51.5% during the same period.

The major histologic type of large bowel cancer is adenocarcinoma, which accounts for 90% to 95% of all large bowel tumors. It is the only histologic type further classified by grade. Grade 1 tumors are the most differentiated, with well-formed tubules and the least nuclear polymorphism and mitoses. Grade 3 tumors are the least differentiated, with only occasional glandular structures, pleomorpehic cells, and a high incidence of mitoses. Grade 2 is intermediate between Grades 1 and 3.

If diagnosed early enough, large bowel adenocarcinoma is highly curable by surgical treatment with minimal morbidity and mortality. In fact, in its initial stage such cancer is virtually 100% curable by surgery. The fact that this common malignancy remains such a deadly killer can be attributed to a number of factors, particularly to diagnostic shortcomings, both in detecting micrometastatic lesions at surgery and in staging colorectal cancer so that appropriate post-surgical adjuvant therapy may be selected.

Colorectal cancer may spread by local invasion, lymphatic extension, hematogenous spread, or implantation. After the initial mucosal growth, a tumor may progress locally in several directions, but usually it protrudes first into the lumen. Mural penetration may result in local failure or peritoneal seeding.

Colorectal cancer first metastasizes to the perirectal nodes at the level of the primary tumor or immediately above it. Next the chain accompanying the superior hemorrhoidal vessels is involved. In later stages of disease, when the hemorrhoidal lymphatics are blocked, there is lateral or downward spread. In colon carcinoma, the normal lymphatic flow is through the lymphatic channels along the major arteries, with three echelons of lymph nodes: pericolic, intermediate, and principal. If tumors lie between two major vascular pedicles, lymphatic flow may drain in either or both directions. If the central lymph nodes are blocked by tumor, lymphatic flow can become retrograde along the marginal arcades proximally and distally. The risk for lymph node metastases increases with increasing tumor grade, as does the number of lymph nodes affected.

The liver is the primary site of hematogenous metastases, followed by the lung. Involvement of other sites in the absence of liver or lung involvement is rare.

Implantation refers to the release of tumor cells from the primary tumor and their deposition on another surface. Implantation has been reported with tumor cells shed intraluminally, from the serosal surface through the peritoneum, and by surgical manipulation and resultant deposition on wound surfaces.

Many variables affect the curability of colorectal cancer. Multivariate analysis indicates the surgical-pathologic stage is the most important. Recurrence patterns are described as local (direct extension), regional (lymphatic and nodal), and peritoneal seeding. The major risk for recurrence in patients with colon cancer remains disseminated disease. The liver is involved in as many as two-thirds of patients who experience recurrence. The risk for locoregional failure varies with the pathologic stage of the primary tumor.

The staging of colorectal carcinoma has been complicated by the fact that it evolved over half a century. Most investigators agree that the most important independent pathologic factor for survival or recurrence after potentially curative surgery is the stage of cancer, which is determined by the depth of penetration through the bowel wall and the presence and number of positive lymph nodes. Other independent factors for survival have included gross appearance, lymphatic vessel invasion, blood vessel invasion, nucleolar organizer regions, character of invasive margin and tumor type, number of mast cells, nuclear shape, sedimentation rate and leukocytosis, lymphocytic infiltration, obstruction, perforation, and rectal bleeding, filtration, infiltrating border (lateral margins), age, grade, venous invasion, gender, obstruction, ploidy, and preoperative carcinoembryonic antigen.

The first practical staging system was the Dukes classification, named after a British pathologist who conducted extensive studies, in the 1930's, on the local invasion and lymphatic spread of rectal cancer. Dukes originally classified rectal tumors from A to C, with stage A indicating penetration into but not through the bowel wall, stage B indicating penetration through the bowel wall, and stage C indicating involvement of lymph nodes, regardless of bowel wall penetration. This system had the virtue of being simple and predictive of prognosis. It has since been modified many times, to reflect finer levels of penetration and nodal metastases, and has been extended to include both colon and rectum. Stage C was further subdivided into C1 (locally positive nodes) and C2 (positive nodes at the point of ligature). Stage A was split into a new stage A (mucosa only) and B1 (into but not through the muscularis propria), and original stage B then became B2. A fourth stage, D, was added to designate disease beyond the limit of surgical resection.

The TNM classification system ranks the primary tumor (T), the regional lymph nodes (N), and distant metastases (M). For example, a T1 tumor invades the submucosa, a T2 tumor the muscularis propria, etc.; N0 indicates an absence of regional node metastases, whereas N1 correlates with 1–3 positive nodes and N2 correlates with 4 or more positive nodes, etc.; and M0 indicates an absence of distant metastases, while M1 indicates that such metastases are present. Any given case of colorectal cancer can thus be described in terms of its TNM status, i.e., $T_xN_xM_x$.

Another staging system, called Astler-Coller, allowed separation of wall penetration and nodal status. The Gunderson-Sosin modification of the Astler-Coller staging system subdivided T3 tumors into those with microscopic ($B2_m$ or $C2_m$) and gross ($B2_{m+g}$ or $C2_{m+g}$) penetration of tumor through the bowel wall. In all pathologic staging systems, particularly those applied to rectal cancer, the abbreviations (m) and (g) may be used: (m) to denote microscopic transmural penetration; (g) or (m+g) to denote transmural penetration visible on gross inspection and confirmed microscopically.

In 1988, the American Joint Committee on Cancer (AJCC) and the Union Internationale Contra le Cancer (UICC) adopted a joint TNM classification scheme taking into account the number of positive nodes and also free mesothelial penetration.

Yet another classification system was introduced in 1987 by Jass and colleagues. Using a Cox regression analysis, they found that the number of positive nodes, whether the invasive border was pushing or infiltrative, the presence of a conspicuous lymphocytic infiltrate, and the absence or presence of transmural penetration were independent prognostic factors. Because the Jass staging system is far more complicated than the modified Dukes and TNM systems, it has not been formally accepted by the National Surgical Adjuvant Breast and Bowel Project (NSABP) or other major clinical groups. The Gastrointestinal Tumor Study Group (GITSG) has also developed a classification system, which shares some of the features of the Jass system.

Not surprisingly, then, the issue of which staging system to use remains a matter of great controversy. The UICC and AJCC TNM staging systems incorporate information regarding the number of positive nodes. In contrast to the Jass and GITSG systems, which stratify by 1 to 4 compared with 5 or more positive nodes, the UICC and AJCC staging systems stratify by 1 to 3 versus 4 or more positive nodes. Further, in contrast to the modified Astler-Coller staging system, the UICC, AJCC, GITSG, and Jass staging systems do not incorporate information regarding the difference between microscopic and gross extension of tumor through the bowel wall. The ongoing controversy over the merits of each of these systems, and their continuing modifications, attests to the fact that no satisfactory system of staging colorectal cancer yet exists. A summary of these staging systems for colorectal carcinoma appears below:

Thus, a reliable and accurate system for the staging of colorectal cancer is urgently needed, whereby available health-care resources may be utilized to their fullest advantage by appropriately identifying those patients whose condition will be improved by the administration of adjuvant chemotherapy, and whereby realistic prognoses may be provided to patients immediately following surgery for primary or recurrent colorectal cancer.

BROAD STATEMENT OF THE INVENTION

Broadly, the present invention is directed to a method for reliably staging adenocarcinomas typified by colorectal cancer in patients who are undergoing surgery therefor. The method includes the administration of a radiolabeled tumor-associated glycoprotein (TAG) antibody (or other equivalent locator) to the cancer patient prior to surgical accession of the patient. Desirably, the present method includes surgical accession with a radiation detection probe for determining tissue exhibiting elevated levels of radiation, as described in U.S. Pat. No. 4,782,840, the disclosure of which is expressly incorporated herein by reference. The preferred radiolabel is $^{125}I$, which is used to label an antibody specific to a high molecular weight glycoprotein called TAG-72, which is present in 85% of colorectal cancers. The preferred antibody is CC49, a murine monoclonal antibody of the $IgG_1$ subclass. With radiolabeled monoclonal antibody CC49, it preferably is administered to the patient approximately 21 days (±4 days) prior to surgery. While a variety of radiation detection devices could be utilized effectively in conjunction with the present invention, the preferred device is a handheld Neoprobe® RIGS® model 1000 portable gamma radiation detector, which forms the basis for the Neoprobe® RIGS® system. Such detector is disclosed in U.S. Pat. Nos. 4,801,803, 4,889,991, 5,070,878, and 5,151,598, the disclosures of which are expressly incorporated herein by reference.

STAGING FOR COLORECTAL CARCINOMA

| Staging System | Confined to Bowel Wall | Penetrates Bowel Wall | Lymph Nodes | Distant Metastatic Site* | Comments |
| --- | --- | --- | --- | --- | --- |
| Dukes | A | B | C | Not Included | Rectum |
| Astler-Coller | A, B1 | B2 | C1 or C2 | D | Colon and Rectum |
| Gunderson Sosin | A, B1 | B2, m + g | C2, C2, m + g | D | Colon and Rectum |
| TNM | T1, 2 NoMo | T3, 4 NoMo | Any T N1, 2, 3 Mo | M/M1 | Colon and Rectum |
| AJCC | T1, 2 NoMo | T3, 4 NoMo | N0 = No Positive Nodes<br>N1 = 1–3 Positive Nodes<br>N2 = 4 or more Positive Nodes | M1 | Colon and Rectum |
| UICC | T1, 2 NoMo | T3, 4 NoMo | N0 = No Positive Nodes<br>N1 = 1–3 Positive Nodes<br>N2 = 4 or more Positive Nodes | M1 | Mesothelial Penetration |
| JASS | T1, 2 NoMo | T3, 4 NoMo | N0 = No Positive Nodes<br>N1 = 1–3 Positive Nodes<br>N2 = 4 or more Positive Nodes | M1 | Lymphocytic Infiltrative Invasive Border (Pushing/Infiltrative) |
| GITSG | T1, 2 NoMo | T3, 4 NoMo | N1 = 1–4 Positive Nodes<br>N2 = 5 or more Positive Nodes | M1 | Colon and Rectum |
| TNM (American Cancer Society) | T1, 2 NoMo | T3, 4 NoMo | N0 = No Positive Nodes<br>N1 = Regional Close Positive Nodes<br>N2 = Regional Distant Positive Nodes<br>N3 = Distant Nodes Around a Major Vessel | M1 | Current System |

*Including nodes outside regional resection.

While the surgeon can use traditional protocols of visualization and palpation for determining tumors to be excised, preferably the '840 system also is employed by the surgeon wherein initial counts are taken with a RIGS® radiation detection probe to identify and localize neoplastic tissue for the surgeon. Following surgical excision of all such tissue which is amenable to excision, the probe is again used to identify any remaining neoplastic tissue or tissue deposits, which may or may not be subjected to further excision attempts. After all possible excision of neoplastic tissue has occurred, final counts are taken with the probe. These counts form the basis of the biostaging system of the present invention. The following equation is then applied to arrive at an integer referred to as an "R Number":

$$R \text{ Number} = (n_1 \times E_1)_1 + (n_2 \times E_2)_2 + (n_3 \times E_3)_3 + (n_4 \times E_4)_4,$$

where, each subscript 1–4 represents an anatomic zone, where 1 is the liver; 2 is the suprapancreatic retroperitoneal area, gastrohepatic ligament, and pancreatic area; 3 is the infrapancreatic retroperitoneal area and colon; and 4 is the rectum and pelvis; each n is a constant, where $n_1=4$, $n_2=2$, $n_3=3$, and $n_4=2$; and each E is the number of tissue deposits identified in each anatomic zone. Finally, the patient is staged based on the R Number.

The R Number has been shown to have excellent prognosticative value in the postsurgical staging of colorectal cancer. Unlike existing staging systems such as the TNM, Dukes, modified Astler-Coller, and Jass systems, the system of the present invention is simple and straightforward and does not rely upon microscopic (e.g., light microscopic) interpretation. The patient's prognosis is determined not by the pathologist, but by the surgeon at the time of surgery. The R Number simply falls into one of three categories, which determines the prognosis, and hence further treatment, as follows:

| R Number | Prognosis |
|----------|-----------|
| 0–1 | Excellent |
| 2–9 | Fair |
| 10> | Poor |

Advantages of the present invention are manifold. The method is simple, convenient, unequivocal in its application, and significantly more accurate than existing biostaging methods. As a result of this increased accuracy, alternative treatment modalities may be more efficiently and judiciously utilized. Patients having an R Number in the first category, 0–1, are surgically cured and do not apparently require any adjuvant therapy. Patients in the third category, with values of 10 and greater, have a poor prognosis which cannot be improved upon by the use of chemotherapy or any other treatment modality. Patients falling into the middle category, with an R Number of 2–9, represent those patients who hopefully may benefit from aggressive adjuvant therapy; ultimately, they will succumb to the cancer or its complications, but alternative treatment will serve to increase their life span. Another advantage of the invention, then, is that it will allow available health-care resources to be allocated in an appropriate fashion. Another advantage is that cancer patients may be more accurately apprised of their condition, thus facilitating planning, eliminating false hopes in cases with poor prognoses, and providing peace of mind in cases with excellent prognoses. These and other advantages will be readily apparent to those skilled in the art based upon the disclosure contained herein.

Figure 1:
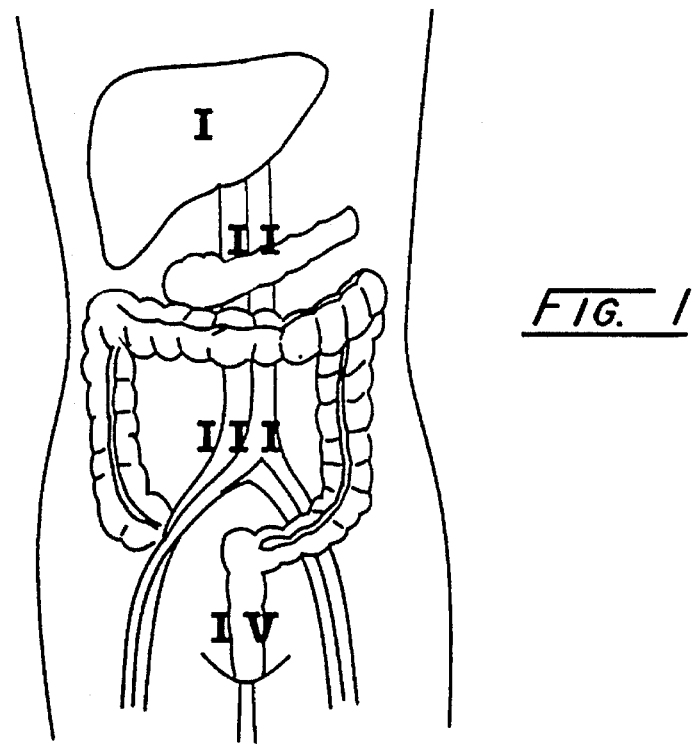
FIG. 1 is a simplified schematic representation of the human abdomen showing the location of the four zones used in calculating the R Number.

The drawings and experimental results reported in the drawings will be discussed in detail below.

DETAILED DESCRIPTION OF THE INVENTION

En bloc surgical resection is the primary treatment approach in patients with colon cancer. Surgical treatment of colon cancer requires excision of an adequate amount of normal colon proximal and distal to the tumor, of adequate lateral margins if the tumor is adherent to a contiguous structure, and of the regional lymph nodes. Pathologic studies indicate that tumor rarely spreads more than 1.2 cm longitudinally beyond the area of gross involvement, and a 5-cm margin is more than adequate. However, removal of intermediate and more central (principal) lymph nodes requires ligation and division of multiple main vascular trunks. Therefore, the extent of the colon resection for potentially curable colon cancer is determined by the biology of local tumor growth and by the associated lymphadenectomy.

Adequate regional lymph node dissection is part of effective therapy for colon cancer. Patients with colon cancer metastatic to regional lymph nodes are in some instances cured with surgery. The paracolic and intermediate lymph nodes are resected routinely, but it is not clear To what extent removal of more central or principal lymph nodes is therapeutic.

Until recently, the in vivo selection of diseased (i.e., tumor bearing) lymph nodes was limited to the surgeon's visual selection and the pathologist's diagnosis. These methods have proven to be unreliable in many cases. While large tumors can be detected intraoperatively by the surgeon by visual inspection and palpation, the primary challenge remains the identification of small subclinical masses.

Because precise tumor margins cannot be determined by conventional surgical procedures, healthy tissue is often removed while varying amounts of neoplastic tissue remain undetected. Staging has traditionally remained almost exclusively within the domain of the pathologist, who acted as final arbiter with regard to malignancy, margins, and other prognostic criteria. Nieroda, et al., "Radioimmunoguided Surgery (RIGS) in Recurrent Colorectal Cancer," *Cancer Detection and Prevention*, vol. 14, issue 6, pp. 651–656 (1990), and "Radioimmunoguided Surgery in Primary Colon Cancer," *Cancer Detection and Prevention*, vol. 15, issue 3, pp. 225–229 (1991), disclose a method for staging of patients afflicted with neoplastic tissue by the RIGS® system using a Neoprobe® RIGS® gamma detecting probe (Neoprobe® and RIGS® are registered trademarks, of Neoprobe Corporation, Columbus, Ohio). Lymph node involvement as determined by such system enables the surgeon and/or oncologist to appropriately stage the patient, e.g., to upstage the patient for adjuvant chemotherapy.

Such staging development is based on U.S. Pat. No. 4,782,840 (the disclosure of which is expressly incorporated herein by reference) which discloses a much improved method for locating, differentiating, and removing neoplasms. Such technique utilizes a radiolabeled antibody and a portable radiation detection probe with the surgeon can use intraoperatively in order to detect sites of increased radioactivity. Such procedure is known as the RIGS system and is successful because of the recognition that tumor detection should be delayed until the blood pool background of circulating radiolabeled antibody has had an opportunity to be cleared from the body so as to enhance the photon emissions or radiation emitted by the tumors compared to surrounding tissue. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be readily determined utilizing a hand-held probe, such as a Neoprobe® RIGS® 1000 radiation detector, as disclosed in U.S. Pat. Nos. 4,893,013; 4,889,991; 5,070,878; and 5,151,598, the disclosures of which are expressly incorporated herein by reference. The first step of the patented method comprises the administration to the patient of an effective amount of a radiolabeled locator which specifically binds a marker produced by or associated with neoplastic tissue. Such "locator" includes a substance which preferentially concentrates at the tumor sides by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778, incorporated herein by reference) and like substances have been developed and may similarly prove efficacious. Biochemistry and genetic engineering may yet produce substances which mimic the function of antibodies in selectively concentrating at the sites of neoplastic tissue, although such substances may not be subsumed within the traditional definition of "antibody." Thus, the terms "locator" was chosen, to include present-day antibodies and equivalents thereof, as well as substances yet to be discovered which mimic antibodies in the inventive method disclosed therein.

The locators (e.g., antibodies) used in the present invention are specific to tumor-associated cell surface antigens. The term "cell surface antigen" as used herein refers to an antigen of the plasma membrane proper and to any part of the tumor cell periphery, including the so-called "fuzzy coat" and extracellular matrix. Most of the antigens demonstrated on the surface of cells have been chemically defined as polysaccharides, glycoproteins, glycolipids, or proteins. A high molecular weight (200,000 to 400,000) glycoprotein, called TAG-72, is present in 85% of colorectal cancers although there is considerable heterogeneity in its expression in the primary tumor, lymph nodes, and distant metastases. TAG-72 occurs widely on human carcinoma cells, including certain human breast carcinoma cell lines, but is absent in normal healthy adult tissues, except secretory-phase endometriam. In addition to colorectal cancers, its presence has been shown in 96% of non-small-cell lung adenocarcinomas, 95% of common epithelial ovarian adenocarcinomas, and a majority of pancreatic, gastric, and esophageal cancers. Thus, the preferred antibodies (or other locators) for use in the staging of colorectal cancers are specific to tumor-associated glycoproteins (TAG), specifically to TAG-72, and are thus referred to as TAG (or, alternatively, anti-TAG) antibodies.

Colorectal adenocarcinomas have their genesis in mucin-secreting cells. Colon cancer cells grow rapidly and continue to secrete mucin, but the mucin is distinctly different from mucin produced by non-malignant cells. It has been found in conjunction with the present invention that TAG antibodies are capable of binding to these abnormal mucins, called sialomucins, thus indicating the presence of cancer cells.

Radiolabeled polyclonal antibodies to a variety of tumor-associated antigens have been used to detect the presence of tumors by gamma scintigraphy in both experimental animal and human studies. However, these polyclonal antibodies directed to membrane-associated antigens have lacked high specificity. Those which were specific for soluble tumor markers yielded images which lacked sensitivity because of high levels of background noise. The advent of monoclonal antibodies has allowed for greater specificity in immunolocalization.

A variety of monoclonal antibodies reactive with human gastrointestinal carcinoma have been described. Of particular note is the monoclonal antibody (MAb) CC49, developed by Schlom and coworkers at the National Cancer Institute. MAb CC49 is a murine monoclonal antibody of the IgG$_1$ subclass which recognizes TAG-72. The antibody is hybridoma-produced and formulated in sterile, pyrogen-free phosphate buffer (pH 7.0). It is available from the Dow Chemical Company, Midland, Mich. CC49 has been selected from a large population of TAG-72—binding antibodies because of its increased reactivity to antigen-positive tissue. This increased reactivity reflects the higher affinity of CC49. The affinity constant of CC49 has been determined to be $16.2 \times 10^9$ $M^{-1}$, which may be as much as eight times higher than that measured for B72.3, another TAG-72 antibody.

With respect to the radiolabel of choice, the ability to use a radiation detection probe that can be placed in immediate adjacency to the lymph node means that lower level energy isotopes are preferred, especially those exhibiting photon emissions of energy levels less than about 300 kev advantageously and preferably less than about 150 kev. $^{125}$I currently is the isotope of choice, although additional low energy isotopes, as disclosed in the '840 patent, may be used as is necessary, desirable, or convenient. Higher energy level radioisotopes (e.g., $^{131}$I) also may be used, although suitable collimation of the radiation detection probe must be employed, which may impede the instrument being facile to the surgeon and limit the areas within the body cavity which can be suitably surveyed. $^{125}$I is preferred because it produces very low energy radiation and optimizes tumor contrast. Also, laparoscopic surgery can only be completed successfully with $^{125}$I.

In addition to radioisotopes emitting gamma radiation, radioisotopes exhibiting beta radiation additionally can be used in conjunction with a probe which can detect beta radiation or positrons. The detection of beta radiation intraoperatively is disclosed, for example, in U.S. Pat. No. 5,008,546, the disclosure of which is expressly incorporated herein by reference. As mentioned supra, the preferred probe is a hand-held Neoprobe® RIGS® model 1000 portable radiation detector, which is designed to detect and quantify gamma radiation. It consists of a sensitive gamma ray detector and a microcomputer-based control unit for fast, easy, and positive location of gamma -emitting isotopes. A "siren" tone is unique to the Neoprobe® RIGS® model 1000 portable detector and enables the user to detect areas of elevated radioactivity while watching the position of the detector probe. The ranging or "squelch" feature windows out the tissue background count that the gamma probe detects during the "squelch" procedure. Areas of activity above this level will cause the siren tone to sound. When the ranging level is established, tissue can be slowly scanned with the probe and areas of radioactivity higher than background will cause the siren to sound. Because of the variability in background counts within the body, it is essential to re-range when a new area is being studied.

Figure 2:
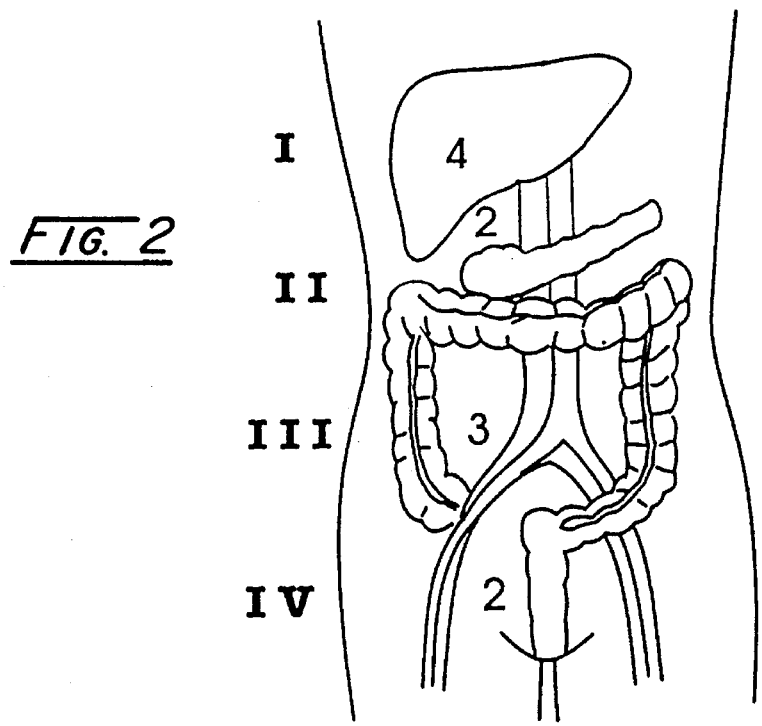
FIG. 2 is a simplified schematic representation of the human abdomen showing the weighting factor applied in each of the four zones shown in FIG. 1.

Experience has shown that patient outcome is, at least in part, dependent upon the location of residual tumor in the patient. Thus, the abdomen is divided into four anatomic zones, as illustrated in FIG. 1, where 1 is the liver; 2 is the suprapancreatic retroperitoneal area, gastrohepatic ligament, and pancreatic area; 3 is the infrapancreatic retroperitoneal area and colon; and 4 is the rectum and pelvis. Residual tumor is identified to be located in one of these four zones. Because patient outcome and residual tumor location are interrelated, residual tumor deposits in each of these four zones are assigned a weighting or factor as depicted in FIG. 2, where zone 1 has a factor of 4, zone 2 a factor of 2, zone 3 a factor of 3, and zone 4 a factor of 2. Thus, residual tumor in zone 1 has a more deleterious affect on patient outcome than residual tumor in the other zones, followed by zone 3, and then zones 2 and 4. Finally, the number of residual tumor deposits, E, in each zone needs to be recorded as experience has shown that the more tumor deposits post-surgery, the more deleterious patient outcome is.

All of the foregoing factors are combined to calculate a value identified as the R Number in accordance with the following formula:

$$R \text{ Number} = (n_1 \times E_1)_1 + (n_2 \times E_2)_2 + (n_{33}{}'E_3)_3 + (n_4 \times E_4)_4$$

The R Number simply falls into one of three categories, which determines the prognosis, and hence further treatment; although, statistically, there is support for combining the prognosis for all R Numbers of greater than 2 which results in only 2 categories. The three category R Number prognosis follows:

| R Number | Prognosis |
|---|---|
| 0–1 | Excellent |
| 2–9 | Fair |
| 10> | Poor |

The data reported herein will amply demonstrate the validity of the R Number staging scheme. It was gathered in accordance with the following experimental procedures. All citations set forth herein are expressly incorporated herein by reference as if fully rewritten herein.

Experimental Procedures

Preparation Of Radiolabeled Antibody

CC49 monoclonal antibody manufactured by the Dow Chemical Company, Midland, Mich., was radiolabeled by the Ohio State University Hospital's Nuclear Medicine Department with sodium iodide $^{125}$I using the 1,3,4,6-tetrachloro-3-alpha-diphenylglycoufil (Iodogen™) method. Unbound iodine was removed by gel filtration chromatography on a cross-linked dextran, Sephadex column. The product was sterilized by filtration through a 0.22 micron filter. The percentage of $^{125}$I bound to protein was determined by high-pressure liquid chromatography (HPLC). A level of $\geq 95\%$ bound was required. Greater than 70% of the antibody must remain immunoreactive after radiolabeling. At least 95% of the product must be homogeneous, i.e., free of aggregates. The sterilized, pyrogen-free radiolabeled antibody was diluted in phosphate-buffered saline (PBS), which was isotonic with respect to sodium. Human serum albumin, USP, was added as stabilizer. The pH of the solution was 7.2±0.2, acceptable for intravenous administration.

Patient Selection and Protocol

This study, which took place between Jul. 1990 and Apr. 1992, utilized the CTEP protocol of the National Cancer Institute. A total of 99 patients were initially enrolled in the study, all of whom had documented colorectal cancer, either primary cancer or recurrent disease. All patients enrolled in the study underwent an extensive preoperative evaluation to eliminate, when possible, those patients with extra-abdominal tumor. Preoperative evaluation included CT scans of the chest, abdomen, and pelvis, as well as a bone scan when deemed necessary. Ten patients were eliminated from the study because the antibody did not localize. Three patients died during surgery, 2 with pulmonary embolisms and 1 with cardiac arrest. Thus, a total of 86 patients were actually evaluated during the course of the study.

Two days prior to administration of the radiolabeled antibody, the patient began treatment with an oral solution of potassium iodide (SSKI at 10 drops twice a day, or KI at 500 mg twice a day) to block uptake of radiolabeled antibody by the thyroid, and this regimen continued for three weeks or until surgery. Once a negative skin test with unlabelled antibody was confirmed, the patient received by intravenous injection 0.1 mg of the CC49 monoclonal antibody labeled with 1 mCi of $^{125}$I diluted in 4 ml of phosphate-buffered saline (PBS) and infused over 5 minutes. All patients were observed for one hour after injection with vital signs recorded every 15 minutes for one hour.

Patients were scheduled for surgery 21 days from the date of injection. Precordial counts of $\leq 20$ (+5) per 2 seconds, as determined by the Neoprobe® RIGS® model 1000 gamma detecting probe, were required at the time of hospital admission as such counts represent a low blood-pool background appropriate for optimum tumor detection. Surgeries were scheduled for patients whose counts were >20 counts per 2 seconds.

Operative Procedure

All patients underwent a surgical exploration of the abdomen. The surgeon inspected and palpated the entire surgical field. Organs explored included the right and left liver lobes, spleen, colon, right and left pelvic walls, bladder, and the ovaries and uterus of female patients. Lymph nodal areas explored included the suprapancreatic retroperitoneal area (Zone 2), infrapancreatic retroperitoneal area (Zone 3), gastrohepatic ligament area (Zone 2), mesenteric and omental area (Zone 3), and the vicinity of the right and left iliac and hypogastric arteries (Zone 4). For each area, the surgeon determined the presence or absence of obvious tumor or suspicious tissue. These findings were reported on case report forms, a portion of which is reproduced in FIG. 3.

The abdomen then was explored again, this time using the hand-held, gamma-detecting probe. All obvious tumors and normal adjacent tissues were counted for two seconds, in triplicate. A siren sound (3 sigma or, standard deviations, criteria set forth in U.S. Pat. No. 4,889,991, the disclosure of which is expressly incorporated herein by reference) was considered a positive finding. The entire surgical field, including the aforementioned areas that were inspected and palpated, were surveyed and counted using the hand-held probe.

All tissue containing tumor deposits as determined by inspection or palpation were resected if possible. Biopsies of tumors were obtained in the event of nonresectable disease. All tissues suspected to contain tumor deposits based solely on noise (siren) obtained by the use of the hand-held probe were biopsied or resected if possible. The bed of resection was surveyed using the hand-held probe to determine residual radioactivity.

The laparotomy involved detailed lymph node sampling. All nodes were grossly characterized as (1) clinically suspicious nodes; (2) RIGS® gamma detector-positive nodes; or (3) clinically negative and RIGS® gamma detector-negative nodes. All lymph nodes obtained underwent histological evaluation, and those containing tumor deposits were noted. Those nodes that were negative for tumor by standard histological examination were studied for tumor cells by more sophisticated and extensive examinations. All such lymph nodes were carefully mapped as to their exact intraabdominal location both before and after surgery so that a pre-surgical and a post-surgical R Number could be calculated.

All patients were evaluated, both by traditional and RIGS® gamma detector techniques, to determine (a) the clinical stage of disease at the time of surgery; and (b) surgical and post-surgical therapeutic patient management.

Tissues obtained at surgery were grossly examined by a pathologist using traditional techniques to stage and determine the extent of disease. The tissues were then re-examined with the Neoprobe® RIGS® model 1000 gamma-detecting probe. Tumor-to-background counts that meet the three sigma criteria were considered a positive finding. Routine histological evaluation was performed on all tissues.

Follow-up

Patients were evaluated one and two years post-surgery for thyroid function and disease status. The classification of these 86 patients according to R Number (hereinafter, RN) is shown in Table 1. A total of 22 patients, 18 with primary colorectal cancer and 4 with recurrent disease, fell into the first category, with an RN of 0–1. Thirty patients, 12 with primary colorectal cancer and 18 with recurrent disease, fell into the second category, with an RN of 2–9. The remaining 34 patients, 11 with primary colorectal cancer and 23 with recurrent disease, fell into the final RN category of 10 and greater. At the end of the study, only 36 of the 86 patients were surviving. In the RN 0–1 category, all of the primary cancer patients, and all but one of the recurrent disease patients, were living. In the RN 2–9 category, between a third and a half of the patients had survived for two years. Finally, in the RN≧10 category, only a very small percentage of patients survived. Table 1 clearly indicates the stratification among these three groups, based on RN.

TABLE 1

| R Number | Colorectal Cancer | | Number Alive | | Percent Alive | |
|---|---|---|---|---|---|---|
| | Primary | Recur. | Primary | Recur. | Primary | Recur. |
| 0–1 | 18 | 4 | 18 | 3 | 100 | 75 |
| 2–9 | 12 | 18 | 5 | 6 | 42 | 33 |
| 10> | 11 | 23 | 1 | 3 | 9 | 13 |
| Total | 41 | 45 | 24 | 12 | 56 | 27 |

Table 2 provides survival data for the 22 patients in category 0–1.

TABLE 2

| RN = 0–1 | |
|---|---|
| Number Dead | Dead at Month |
| 1 | 16 |

Table 3 provides survival data for the 30 patients in category 2–9.

TABLE 3

| RN = 2–9 | |
|---|---|
| Number Dead | Dead at Month |
| 2 | 6 |
| 2 | 8 |
| 1 | 9 |
| 1 | 10 |
| 1 | 11 |
| 1 | 12 |
| 2 | 13 |
| 1 | 18 |
| 5 | 20 |
| 1 | 22 |
| 2 | 25 |
| 1 | 26 |

Table 4 provides survival data for the 34 patients in category 10>.

TABLE 4

| RN = 10> | |
|---|---|
| Number Dead | Dead at Month |
| 1 | 1 |
| 3 | 3 |
| 4 | 4 |
| 1 | 5 |
| 2 | 8 |
| 2 | 9 |
| 3 | 10 |

TABLE 4-continued

| RN = 10> | |
|---|---|
| Number Dead | Dead at Month |
| 2 | 11 |
| 3 | 12 |
| 2 | 13 |
| 1 | 14 |
| 1 | 15 |
| 1 | 16 |
| 1 | 17 |
| 1 | 19 |
| 1 | 20 |
| 2 | 28 |

Figure 3:
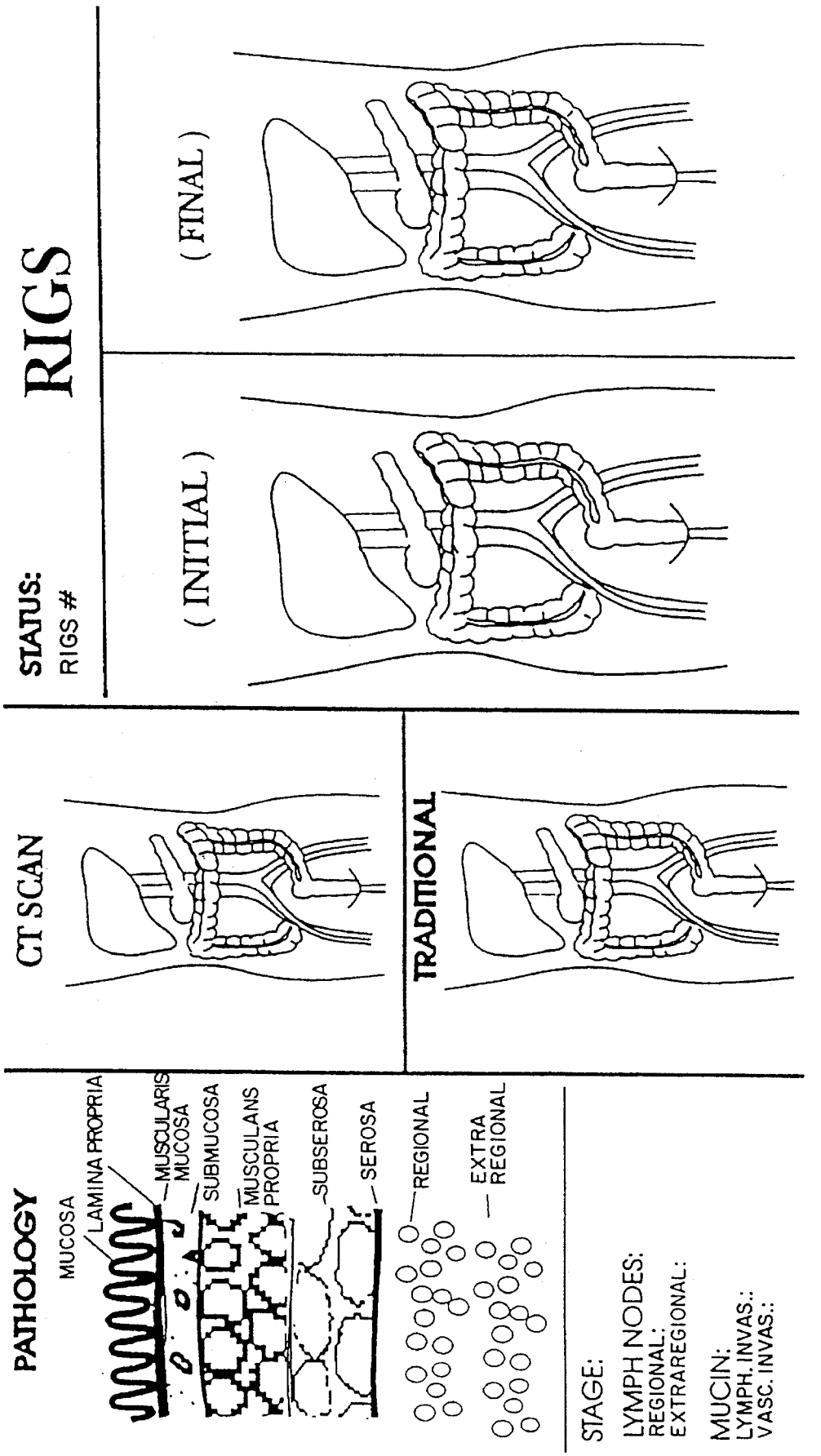
FIG. 3 is a portion of the case report forms used to collect the patient data reported herein.
Figure 4:
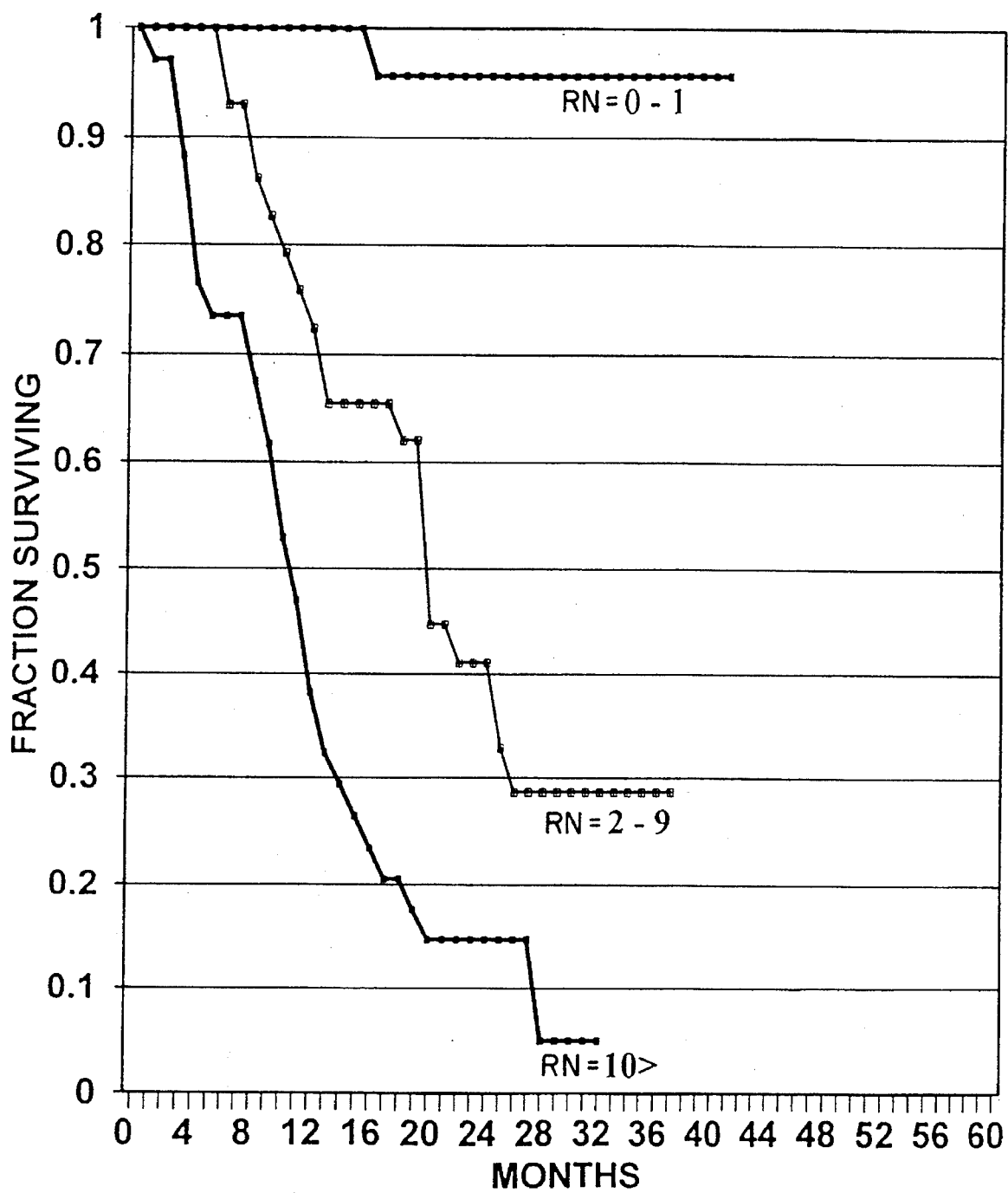
FIG. 4 graphically depicts primary and recurrent colorectal cancer patient survival data as a function of time following surgery staged by the R Number staging scheme.

The great disparity among these three groups can be seen in FIG. 4, wherein graphical depictions of the survival data from FIGS. 1–3 are superimposed.

Thus, it can be seen that patients having a R Number in the first category, 0–1, have an excellent prognosis. Patients in the third category, with values of 10 and greater, have a dismal prognosis. Patients falling into the middle category, with a R Number of 2–9, have a prognosis somewhere in the middle. As stated supra, these are the patients who will benefit from aggressive adjuvant therapy; although, they ultimately will succumb to the cancer or its complications. Alternative treatment may serve to increase their life span.

In contrast to the R Number classification scheme of the present invention, the primary colorectal patients also were staged using traditional techniques and compared to the inventive R Number classification scheme for the primary colorectal patients based on the data set forth above. Stages I and II mean that no lymph nodes were found, stage III indicates involvement of lymph nodes, and stage IV designates disease beyond the limit of surgical resection. The results of this staging are shown in Table 5.

TABLE 5

| Traditional Staging | | | |
|---|---|---|---|
| Stage | No. of Patients | Alive | Percent Alive |
| I/II | 15 | 13 | 87 |
| III | 11 | 8 | 73 |
| IV | 15 | 3 | 20 |

Table 6 provides survival data for the 15 patients classified as Stage I/II.

TABLE 6

| Stage I/II | |
|---|---|
| Number Dead | Dead at Month |
| 1 | 8 |
| 1 | 25 |

Table 7 provides survival data for the 11 patients classified as Stage III.

TABLE 7

| Stage III | |
|---|---|
| Number Dead | Dead at Month |
| 1 | 13 |
| 1 | 25 |
| 1 | 26 |

Table 8 provides survival data for the 15 patients classified as Stage IV.

TABLE 8

| Stage IV | |
|---|---|
| Number Dead | Dead at Month |
| 1 | 1 |
| 2 | 3 |
| 3 | 4 |
| 2 | 8 |
| 1 | 11 |
| 1 | 13 |
| 2 | 20 |

Figure 5:
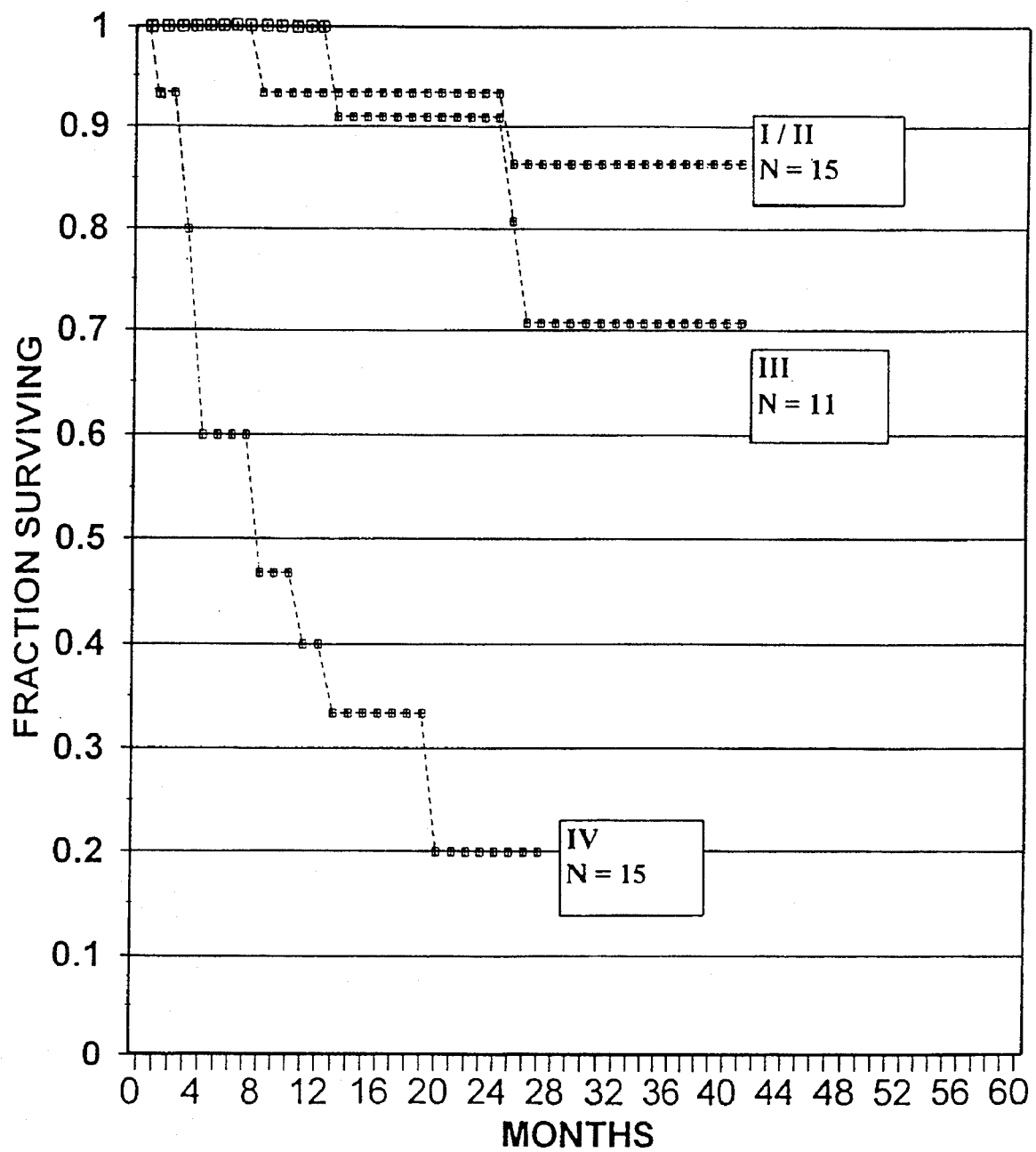
FIG. 5 graphically depicts patient survival data as a function of time following surgery for primary colorectal cancer patients staged traditionally.

Data for all three groups can be seen in FIG. 5, wherein graphical depictions of the survival data from Tables 6–8 are superimposed. While overall differences among the three groups are apparent, with stage I/II having a better prognosis than stage III, and so forth, stratification is much less apparent and there is considerable overlap among the groups.

Survival data in Tables 1–4 (inventive R Number staging scheme) for the primary colorectal patients only is set forth below in Tables 9–11.

TABLE 9

| RN = 0–1 for Primary Colorectal Patients | |
|---|---|
| Number Dead | Dead at Month |
| 0 | — |

TABLE 10

| RN = 2–9 for Primary Colorectal Patients | |
|---|---|
| Number Dead | Dead at Month |
| 2 | 8 |
| 1 | 13 |
| 1 | 20 |
| 2 | 25 |
| 1 | 26 |

TABLE 11

| RN ≧10 for Primary Colorectal Patients | |
|---|---|
| Number Dead | Dead at Month |
| 1 | 1 |
| 2 | 3 |
| 1 | 8 |
| 1 | 11 |
| 1 | 13 |

TABLE 11-continued

| RN ≧10 for Primary Colorectal Patients | |
|---|---|
| Number Dead | Dead at Month |
| 1 | 20 |

Figure 6:
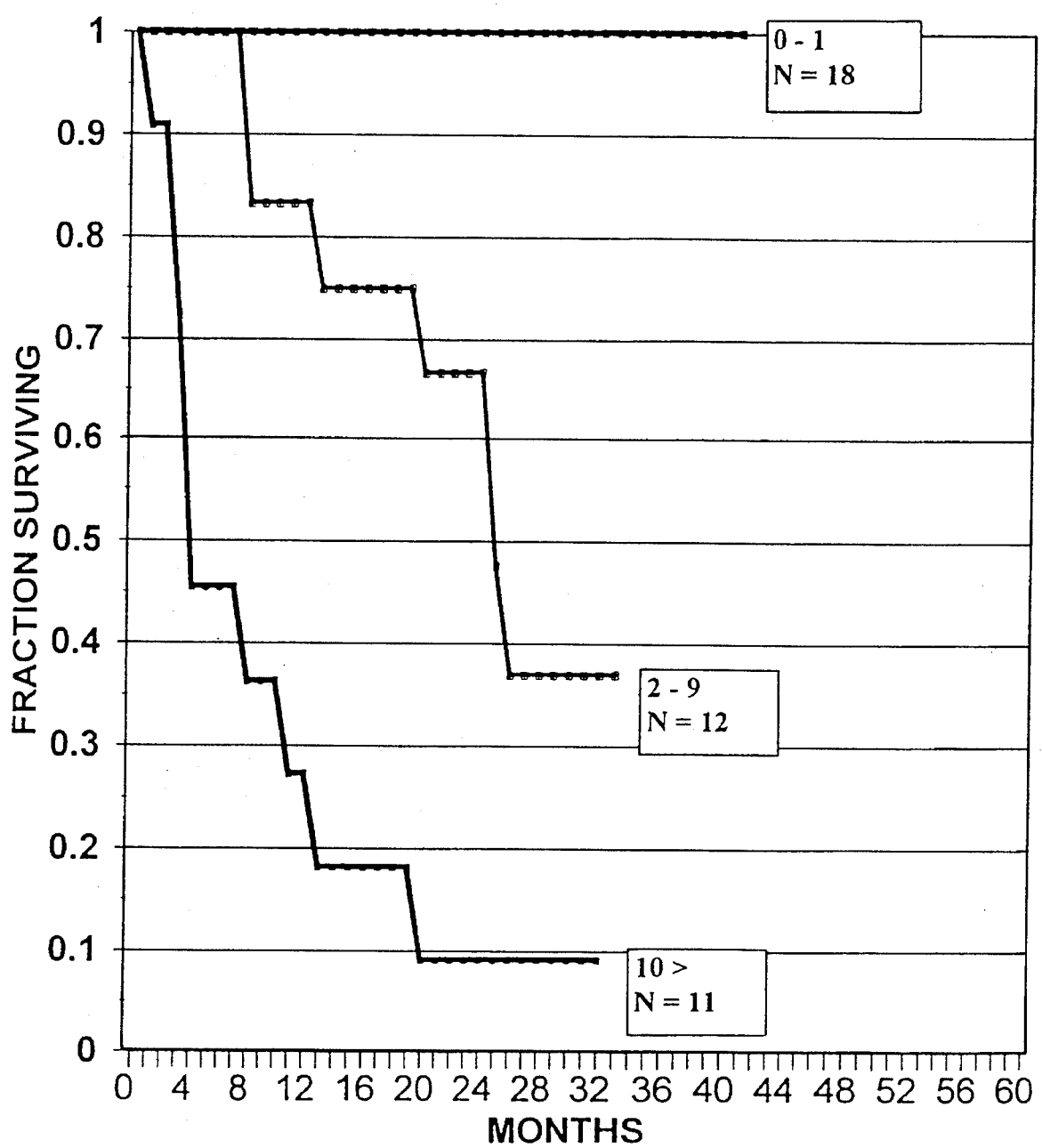
FIG. 6 graphically depicts patient survival data as a function of time following surgery for primary colorectal cancer patients staged by the R Number staging scheme.
Figure 7:
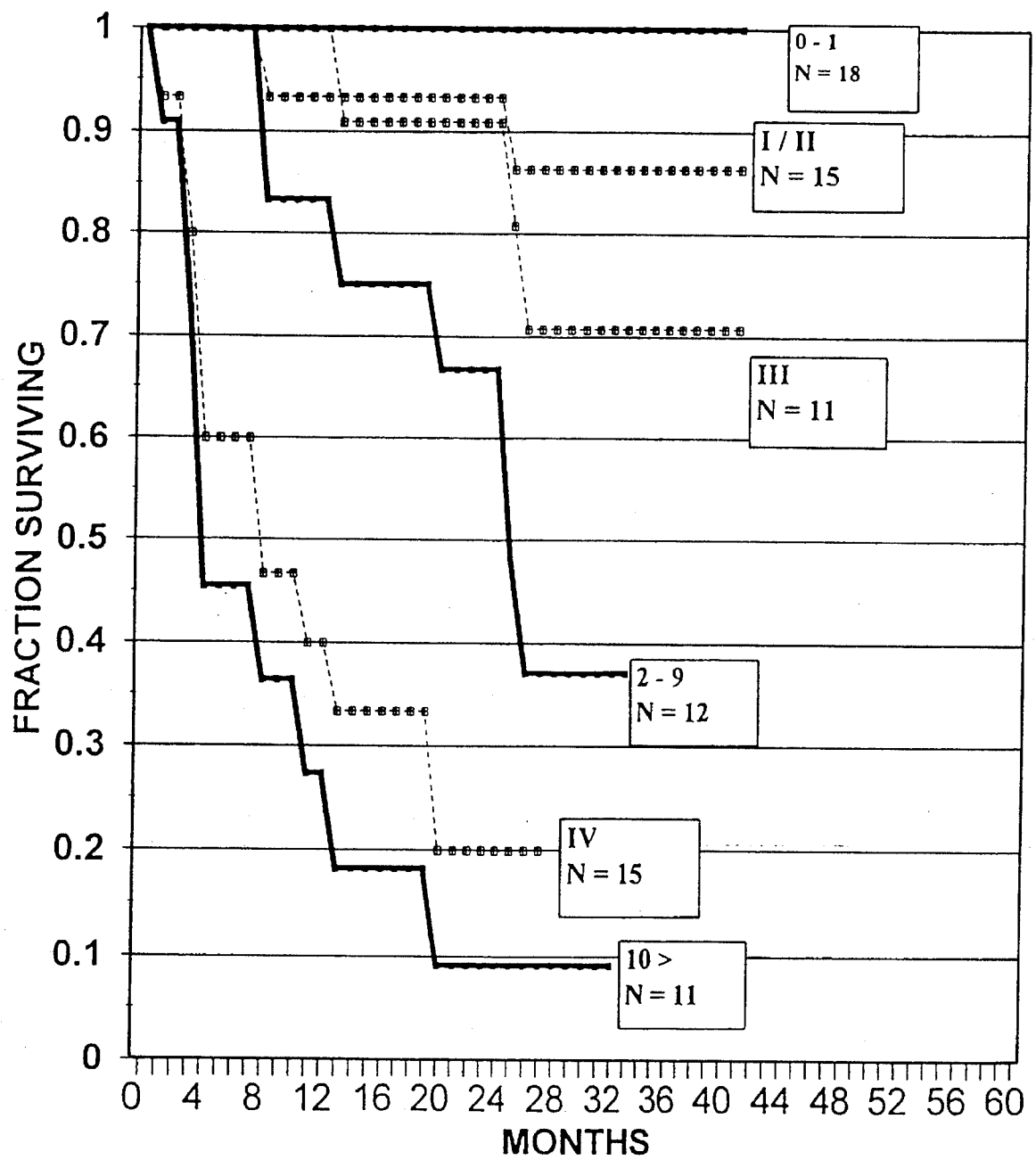
FIG. 7 graphically compares FIGS. 5 and 6.

FIG. 6 graphically depicts the results displayed in Tables 9–11. A comparison of traditional staging and the inventive R Number staging is illustrated in FIG. 7 which overlays FIGS. 5 and 6.

The survival data for the traditionally staged and the inventive R Number staged primary colorectal patients are compared below in Table 12.

TABLE 12

| Traditional Staging | | R Number Staging | |
|---|---|---|---|
| Stage | No. Patients | R Number | No. Patients |
| I/II | 15 | 0–1 | 18 |
| III | 11 | 2–9 | 12 |
| IV | 15 | 10> | 11 |

Placing the traditionally-staged patients under the R Number staging scheme results in a realignment of patients as set forth in Table 13.

TABLE 13

| Stage | No. Patients | Percent | |
|---|---|---|---|
| R Number = 0–1 | | | |
| I/II | 9 | 50 | N = 18 |
| III | 7 | 39 | |
| IV | 2 | 11 | |
| R Number = 2–9 | | | |
| I/II | 6 | 50 | N = 12 |
| III | 3 | 25 | |
| IV | 3 | 25 | |
| R Number = 10> | | | |
| I/II | 0 | 0 | N = 11 |
| III | 1 | 9 | |
| IV | 10 | 91 | |

Figure 8:
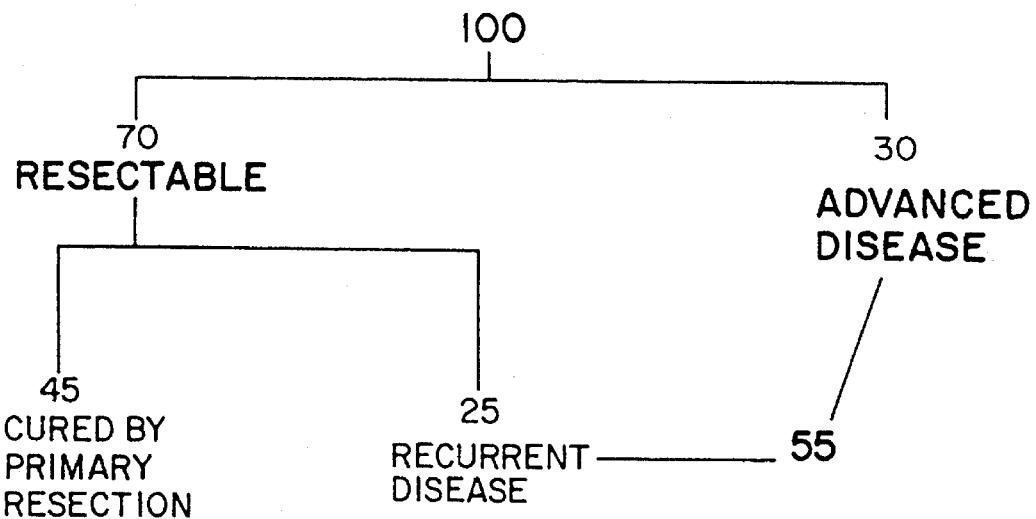
FIG. 8 is a partial reproduction of FIG. 30-1 from DeVita, et al. entitled "Colorectal Patients, End Results of Treatment"

Data on colorectal patients reported by DeVita, et al., *Cancer: Principles & Practice of Oncology*, 4th Edition, J.B. Lippincott Company, Philadelphia, Pa. (1993) (expressly incorporated herein by reference) in FIG. 30-1 (page 930) is partially reproduced as FIG. 8. DeVita comments on these results: "FIG. 30-1 provides an overview of the end results of treatment of patients with colon and rectal adenocarcinoma. It demonstrates the need for improved earlier diagnosis and control of micrometastatic disease." Id at 929.

Figure 9:
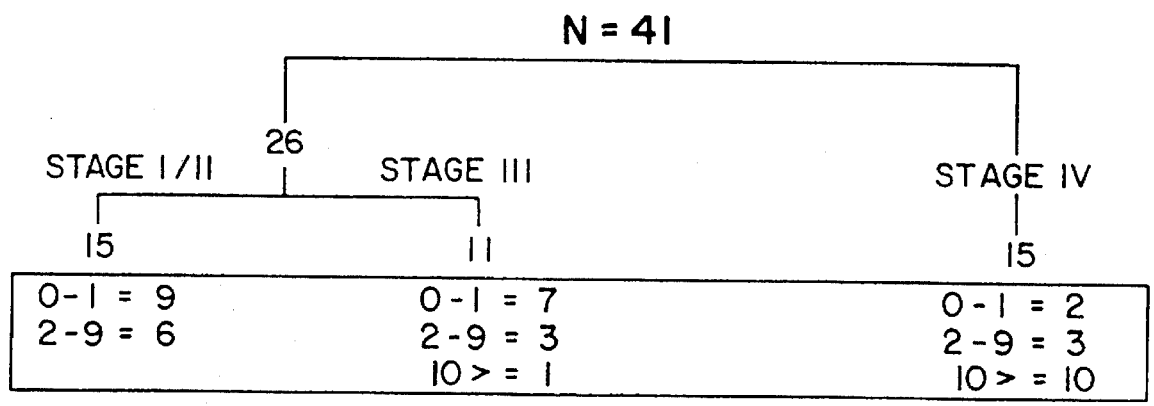
FIG. 9 presents the data of Tables 5–8 in the FIG. 8 format entitled "Colorectal Patients, Traditional"

The data presented at Tables 5–8 are set forth in the DeVita format at FIG. 9. However, clearly evident from these results are numerous plaguing questions. How does the physician know which patients may need chemotherapy (or other treatment modality) and which do not? Based on these traditional staging results, six patients (33%) of the fifteen patients in Stage I/II would be candidates for immediate adjuvant chemotherapy according to the inventive R Number staging scheme. In Stage III, seven patients potentially do not need further chemotherapy as all disease now has cleared; yet, these patients will receive chemotherapy. In Stage IV, all patients need additional therapy; yet, in two of the patients all disease now has cleared.

Figure 10:
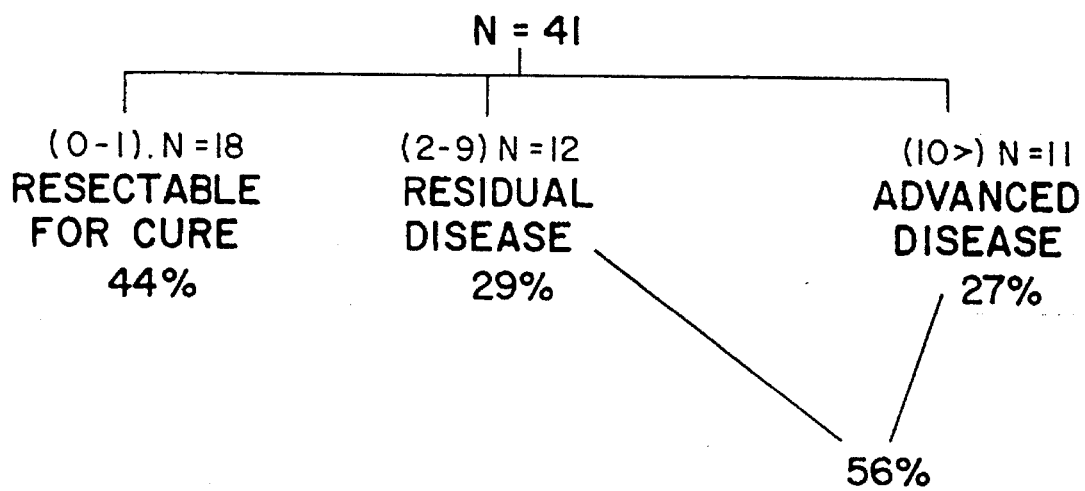
FIG. 10 presents the data of Tables 6–11 in the FIG. 8 format entitled "Colorectal Patients, R Number Staging"

The data presented at Tables 6–11 are set forth in the DeVita format at FIG. 10. These results should be compared to FIG. 8 of DeVita. Clearly, the R Number staging scheme tracks the experience data reported by DeVita quite remarkably, and much more accurately than the traditional staging data.

As a result of the confusion and uncertainty as to the actual prognosis of any given cancer patient using traditional staging techniques, adjuvant therapy ordinarily is administered indiscriminately to all post-surgical colorectal cancer patients. By virtue of the more accurate staging method of the present invention, unnecessary medical and health insurance costs may be avoided, since only those patients who will be helped by adjuvant therapy need undergo the expense, inconvenience, and potential side effects of same. Moreover, patients that do not need further modalities of treatment will receive none, thus improving the quality of their lives while reducing costs to them.

It is to be noted that traditional cancer classification or staging is based on the extent and location of the cancer before surgery. The R Number staging scheme of the present invention, however, is based on the extent and location of the cancer post-surgery. In fact, the R Number staging scheme has been applied to the patients cited above before surgical excision of the tumor burden and correlation with survival was absent (as with traditional staging techniques). Thus, a fundamental discovery reported herein is that staging should be based on the extent (number of tumor sites) remaining after surgery and the location of such sites with a weighting being assigned to various zones in the abdomen. The weighting assigned to the various zones for use in calculating the R Number was empirically derived, but has proven to be quite accurate. Of importance is that the location of residual (nonresectable) tumor in patients impacts their prognosis and their staging.

Figure 11:
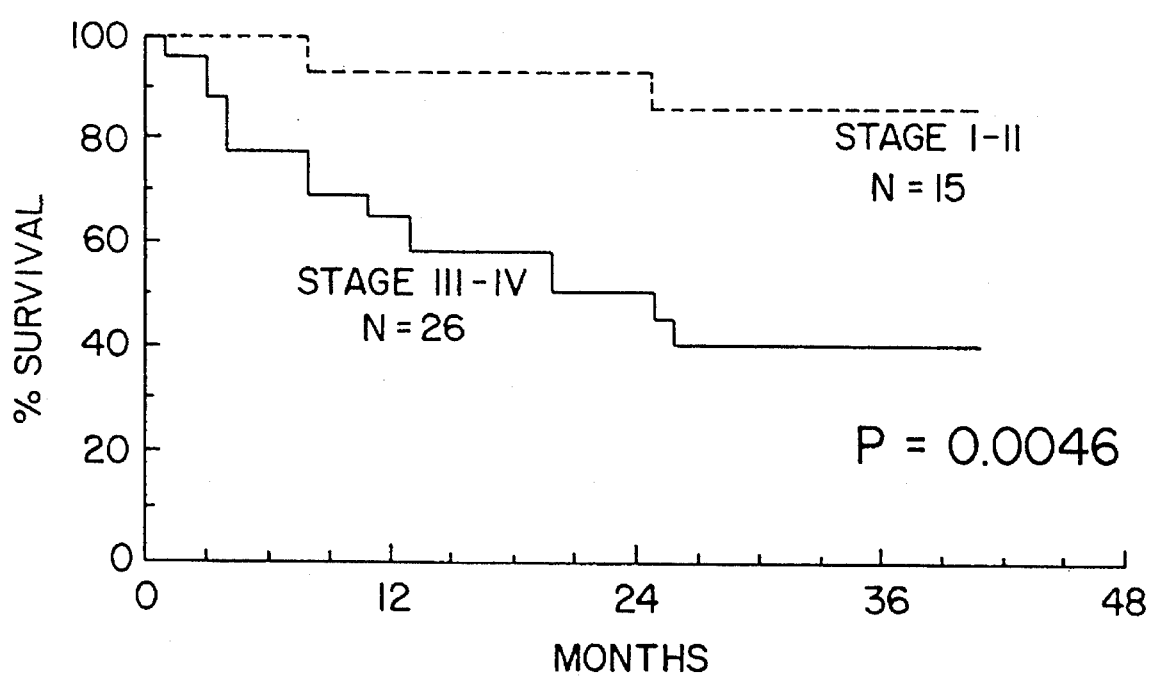
FIG. 11 is FIG. 5 with Stages III and IV combined.
Figure 12:
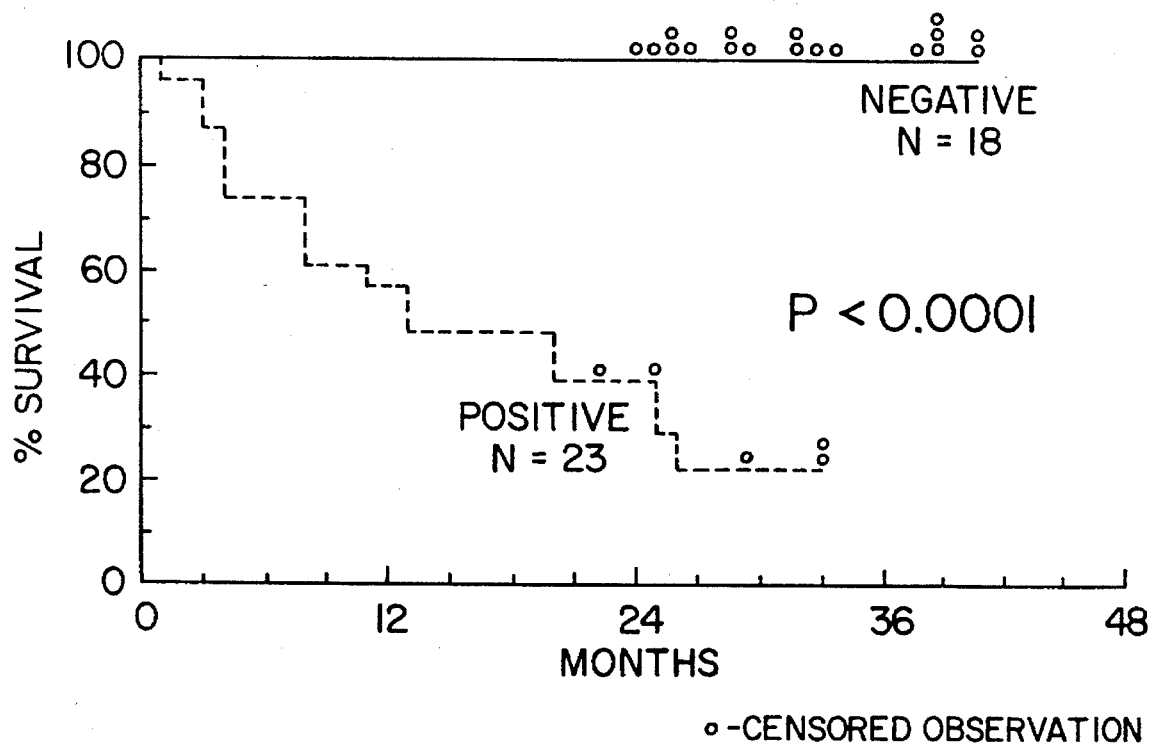
FIG. 12 is FIG. 6 with R Numbers=2–9 and 10>combined.

The impact of the R Number may be appreciated when it is learned that for the primary colorectal patients reported above staged traditionally with 15 patients being Stage I/II and 26 patients being Stage III/IV, the log rank comparison is P=0.0046 (Kaplan-Meyer Survival Curve, Lee-Desu statistic); while for the patients staged with an R Number with 18 patients being negative (RN=0–1) and 23 patients being positive (RN=2>), the log rank comparison is P<0.0001, as can be seen by reference to FIGS. 11 and 12. Of the 18 patients with RN=0–1, 1 has pelvic recurrence and 17 are NED (no evidence of disease). However, of the 6 surviving patients with RN=2>, 2 patients have recurrent disease (these patients have been reported out as not resectable), 1 has bilateral pulmonary metastases, 1 has rising CEA, and 2 are NED. Post-surgical residual tumor results in patient death, as evidenced by 3-year survival data of the patients.

The disclosure of all citations herein is expressly incorporated by reference as if fully written herein.

I claim:

1. A method for staging a patient undergoing surgery for suspected primary or recurrent adenocarcinoma, which comprises the steps of:

(a) administering to said patient an effective amount of a radiolabeled locator specific for a tumor-associated glycoprotein having a molecular weight of 200,000 to 400,000, and labeled with a radioactive isotope exhibiting photon emissions of select energy levels;

(b) delaying said surgery for a time interval following said administering for permitting said labeled locator to preferentially concentrate in any adenocarcinoma tissue present in said patient and for the unbound labeled locator in the blood pool to be cleared to a blood pool background level, so as to increase the ratio of photon emissions from adenocarcinoma tissue to background photon emissions in said patient;

(c) surgically accessing an operative field of said patient;

(d) surgically excising surgically-accessible adenocarcinomic tissue;

(e) following step (d), positioning within said operative field a radiation detection probe having perceptible output pulses responsive to photon emissions and readout means responsive to said output pulses, to identify tissue a number and location of tissue deposits exhibiting elevated levels of radiation;

(f) recording the number and location of the tissue deposits identified in step (e);

(g) calculating an R Number in accordance with the following formula:

$$R \text{ Number} = (n_1 \times E_1)_1 + (n_2 \times E_2)_2 + (n_3 \times E_3)_3 + (n_4 \times E_4)_4,$$

where, each subscript 1–4 represents and anatomic zone, where 1 is the liver; 2 is the suprapancreatic retroperitoneal area, gastrohepatic ligament, and-pancreatic area; 3 is the infrapancreatic retroperitoneal area and colon; and 4 is the rectum and pelvis; each n is a constant, where $n_1=4$, $n_2=2$, $n_3=3$, and $n_4=2$; and each E is the number of tissue deposits identified in each anatomic zone; and (h) staging the patient based on the R Number determined in step (g).

2. The method of claim 1, wherein said tumor-associated glycoprotein is TAG-72.

3. The method of claim 1, wherein said radiolabeled locator is an antibody.

4. The method of claim 3, wherein said antibody is a monoclonal antibody.

5. The method of claim 4, wherein said monoclonal antibody is CC49.

6. The method of claim 5, wherein said time interval for delaying surgery is 17 to 25 days following administration of said radiolabeled antibody.

7. The method of claim 6, further including taking precordial counts of said patient after step (a) and and delaying surgery in step (b) until said precordial counts of ≦20 per 2 seconds are obtained.

8. The method of claim 1, wherein said radioactive isotope is $^{125}$I.

9. The method of claim 1, wherein said perceptible output pulses comprise sound.

10. The method of claim 9, wherein said sound is audible only when tissue radioactivity is higher than background radioactivity by three standard deviations (sigma).

11. A method for staging a patient undergoing surgery for suspected primary or recurrent adenocarcinoma, which comprises the steps of:

(a) administering to said patient an effective amount of a radiolabeled antibody specific for a tumor-associated glycoprotein having a molecular weight of 200,000 to 400,000, and labeled with a radioactive isotope exhibiting photon emissions of select energy levels;

(b) delaying said surgery for a time interval following said administering in step (a) for permitting said labeled antibody to preferentially concentrate in any neoplastic tissue present in said patient and for any unbound labeled antibody in the blood pool to be cleared to a blood pool background level, so as to increase the ratio of photon emissions from neoplastic tissue to background photon emissions in said patient;

(c) surgically accessing an operative field of said patient;

(d) determining a background photon emission count for tissue within said operative field which is to be examined for neoplastic tissue;

(e) manually positioning within said operative field a hand-held radiation detection probe having perceptible output pulses responsive to photon emissions and readout means responsive to said output pulses, to identify tissue deposits exhibiting elevated levels of radiation;

(f) surgically excising all said tissue deposits which are amenable to excision and which exhibits elevated levels of radiation;

(g) recording the number and location of the tissue deposits identified in step (f) that are not excised;

(h) calculating an R Number in accordance with the following formula:

$$R \text{ Number} = (n_1 \times E_1)_1 + (n_2 \times E_2)_2 + (n_3 \times E_3)_3 + (n_4 \times E_4)_4,$$

where, each subscript 1–4 represents an anatomic zone, where 1 is the liver; 2 is the suprapancreatic retroperitoneal area, gastrohepatic ligament, and pancreatic area; 3 is the infrapancreatic retroperitoneal area and colon; and 4 is the rectum and pelvis; each n is a constant, where $n_1=4$, $n_2=2$, $n_3=3$, and $n_4=2$; each E is the number of tissue deposits identified in step (g) in each anatomic zone; and (i) staging the patient based on the R Number determined in step (g).

12. The method of claim 11, wherein said tumor-associated glycoprotein is TAG-72.

13. The method of claim 11, wherein said antibody is a monoclonal antibody.

14. The method of claim 13, wherein said monoclonal antibody is CC49.

15. The method of claim 14, wherein said time interval for delaying surgery is 17 to 25 days following administration of said radiolabeled antibody.

16. The method of claim 15 further including taking precordial counts of said patient after step (a) and and delaying surgery in step (b) until said precordial counts of ≦20 per 2 seconds are obtained.

17. The method of claim 14, wherein said radioactive isotope is $^{125}$I.

18. The method of claim 11, wherein said radioactive isotope is $^{125}$I.

19. The method of claim 11, wherein said perceptible output pulses comprise sound.

20. The method of claim 19, wherein said sound is audible only when tissue radioactivity is higher than background radioactivity.

* * * * *